United States Patent
Tan et al.

(10) Patent No.: US 11,103,681 B2
(45) Date of Patent: Aug. 31, 2021

(54) CAPS FOR NEEDLES AND CATHETERS

(71) Applicant: B. Braun Melsungen AG, Melsungen (DE)

(72) Inventors: Aik Aun Tan, Penang (MY); Wen Jenn Lim, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 359 days.

(21) Appl. No.: 15/518,450

(22) PCT Filed: Oct. 15, 2015

(86) PCT No.: PCT/EP2015/073917
§ 371 (c)(1),
(2) Date: Apr. 11, 2017

(87) PCT Pub. No.: WO2016/059172
PCT Pub. Date: Apr. 21, 2016

(65) Prior Publication Data
US 2017/0246429 A1    Aug. 31, 2017

Related U.S. Application Data

(60) Provisional application No. 62/064,916, filed on Oct. 16, 2014.

(51) Int. Cl.
*A61M 25/06* (2006.01)
*A61M 25/02* (2006.01)
(Continued)

(52) U.S. Cl.
CPC ........ *A61M 25/0637* (2013.01); *A61M 25/02* (2013.01); *A61M 25/0606* (2013.01);
(Continued)

(58) Field of Classification Search
CPC ........ A61M 2025/0253; A61M 25/002; A61M 25/02; A61M 25/0606; A61M 25/0618;
(Continued)

(56) References Cited

U.S. PATENT DOCUMENTS 3,434,473 A * 3/1969 Smith ................. A61M 5/3202
604/117
5,169,391 A * 12/1992 Vogel ................. A61M 5/3213
604/177

(Continued)

FOREIGN PATENT DOCUMENTS

CN    101573153 A    11/2009
CN    101790396 A    7/2010
(Continued)

OTHER PUBLICATIONS

International Search Report and Written Opinion on corresponding PCT application (PCT/EP2015/073917) from International Searching Authority (EPO) dated Mar. 21, 2016.
(Continued)

*Primary Examiner* — Lauren P Farrar
*Assistant Examiner* — Hamza A Darb
(74) *Attorney, Agent, or Firm* — Klein, O'Neill & Singh, LLP

(57) ABSTRACT

Needle assemblies are disclosed having a multi-purpose protective cap. The needle assemblies can embody a catheter assembly having a catheter hub and a catheter tube or a hypodermic needle mounted on a needle hub. The multi-purpose cap includes a first section covering the needle and a second section having a base portion for covering a hub, such as a needle hub or a catheter hub. The first section and the second section are separable from one another along a detachment line and the second section is re-useable as a securement device.

21 Claims, 17 Drawing Sheets

(51) Int. Cl.
  *A61M 25/00* (2006.01)
  *A61M 5/32* (2006.01)
  *A61M 5/50* (2006.01)
(52) U.S. Cl.
  CPC .... *A61M 25/0618* (2013.01); *A61M 25/0631* (2013.01); *A61M 5/3202* (2013.01); *A61M 5/5086* (2013.01); *A61M 25/002* (2013.01); *A61M 2025/0253* (2013.01)
(58) Field of Classification Search
  CPC .......... A61M 25/0631; A61M 25/0637; A61M 5/3202; A61M 5/5086; A61M 5/158; A61B 5/15074; A61B 5/150717
  See application file for complete search history.

(56) References Cited

U.S. PATENT DOCUMENTS

| | | | |
|---|---|---|---|
| 5,290,265 A | | 3/1994 | Davis et al. |
| 5,584,813 A | | 12/1996 | Livingston et al. |
| 8,226,604 B2* | | 7/2012 | Madin .................. A61M 5/3216 604/110 |
| 8,323,251 B2* | | 12/2012 | West ..................... A61B 5/1405 206/365 |
| 2008/0135443 A1 | | 6/2008 | Frojd et al. |
| 2009/0187153 A1* | | 7/2009 | West ................ A61B 5/150587 604/263 |

FOREIGN PATENT DOCUMENTS

| | | | |
|---|---|---|---|
| FR | 2118743 A5 | 7/1972 | |
| JP | H04-501671 A | 3/1992 | |
| JP | 2010-533020 A | 10/2010 | |
| JP | 2013-528424 A | 7/2013 | |
| WO | WO 2011/138746 A1 | 11/2011 | |

OTHER PUBLICATIONS

Office Action on corresponding foreign application (CN Application No. 201580055939.0) from the National Intellectual Property Administration, P.R. China dated Aug. 30, 2019.
Office Action on corresponding foreign application (AU Application No. 2015332645) from the Australian Patent Office dated Jun. 12, 2019.
Office Action on corresponding foreign application (JP Application No. 2017-515140) from the Japanese Patent Office dated May 14, 2019.
Examination Report on corresponding foreign application (AU Application No. 2015332645) from IP Australia dated Mar. 11, 2020.
Preliminary Examination Report on corresponding foreign application (BR Application No. BR112017007698-5) from Brazilian Patent Office dated Mar. 31, 2020.
Decision of Rejection on corresponding foreign application (JP Application No. 2017-515140) from the Japan Patent Office dated Jan. 7, 2020.
Notice of Acceptance on corresponding foreign application (AU Application No. 2015332645) from IP Australia dated Jun. 17, 2020.
Office Action on corresponding foreign application (JP Application No. 2020-081732) from Japan Patent Office dated Feb. 9, 2021.

* cited by examiner

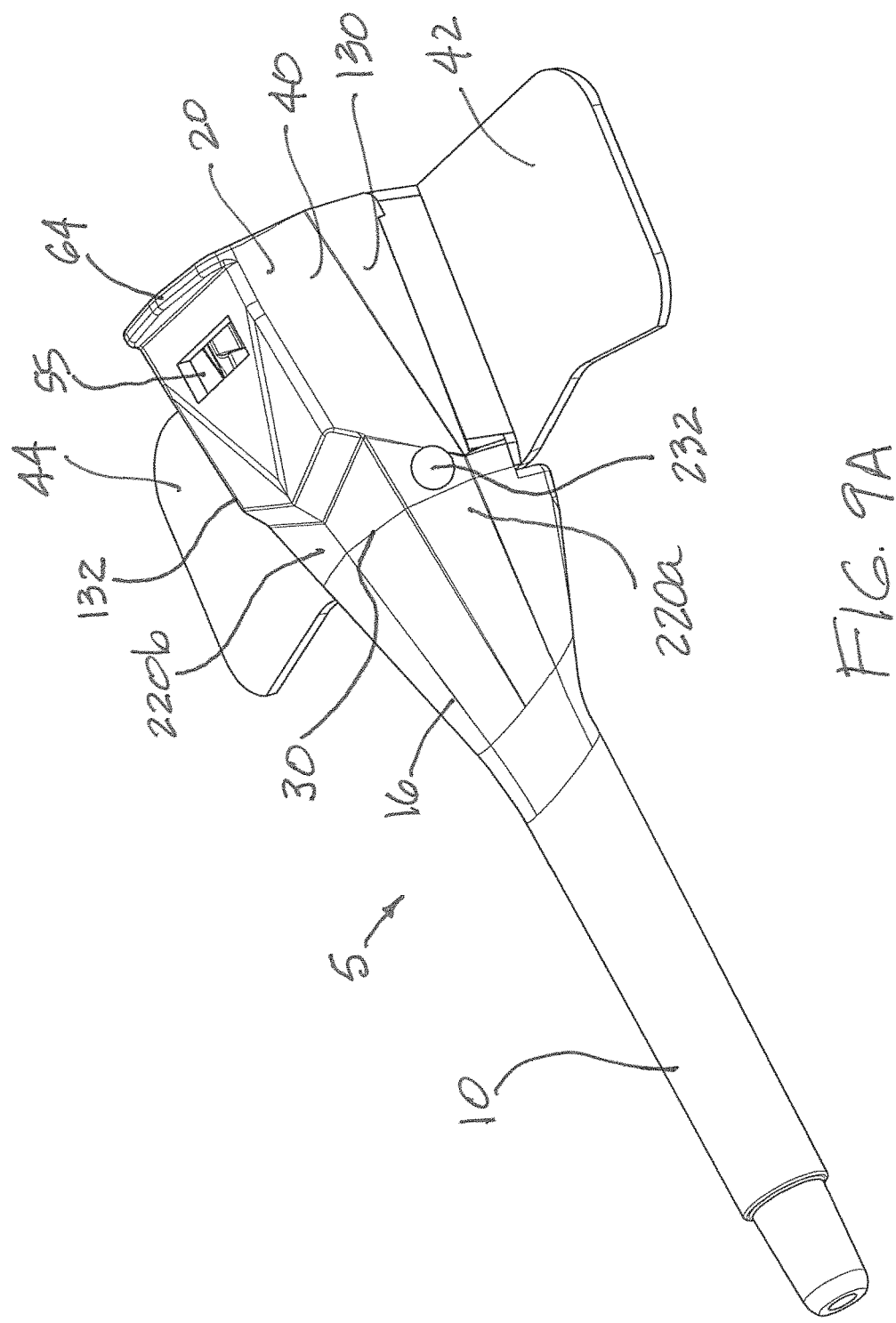

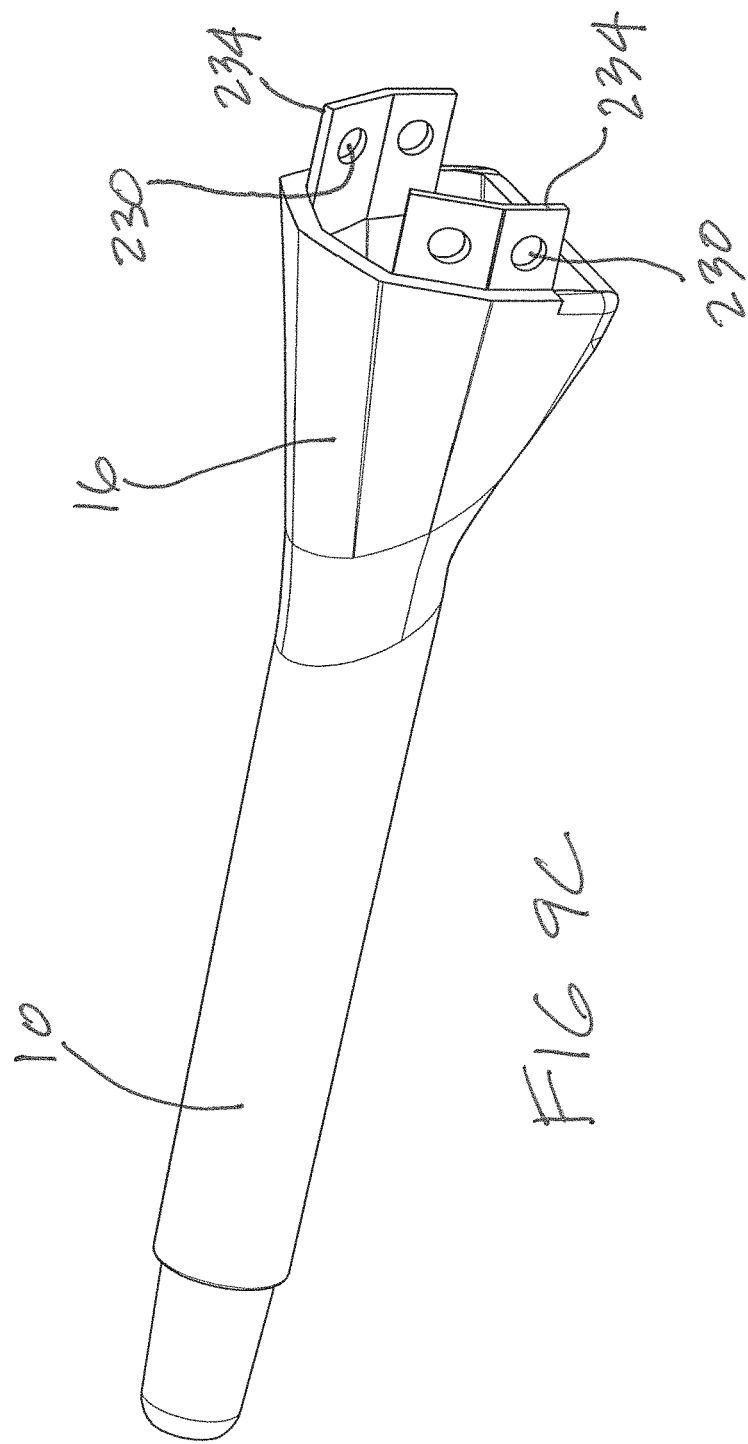

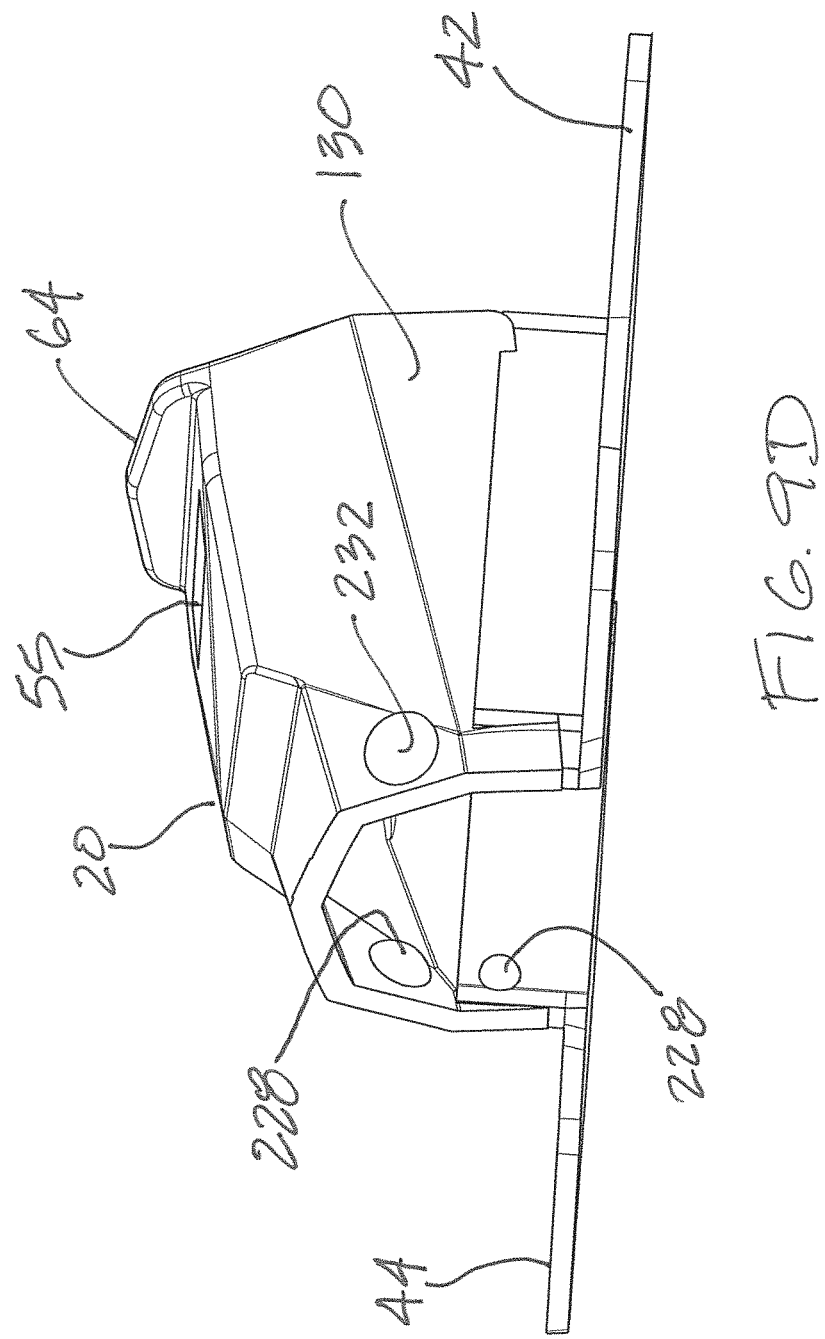

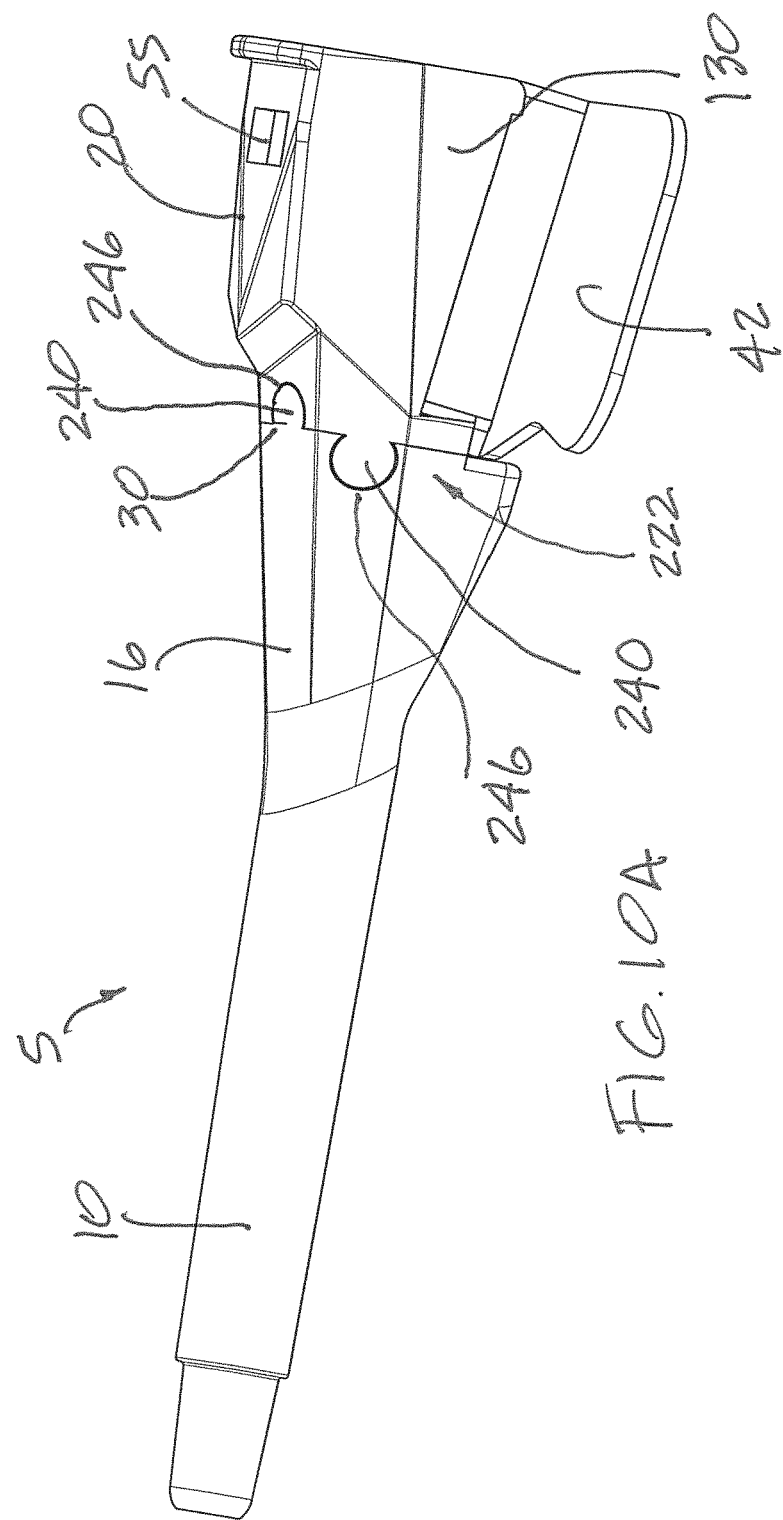

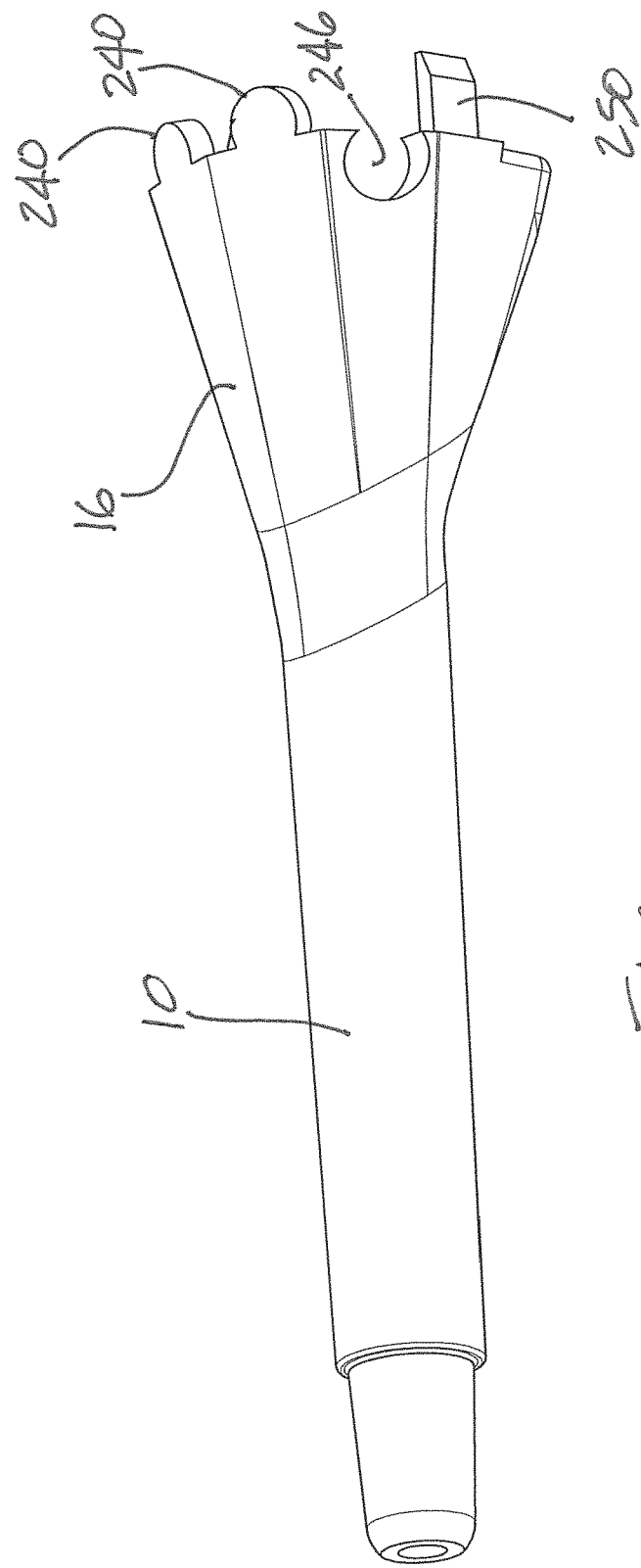

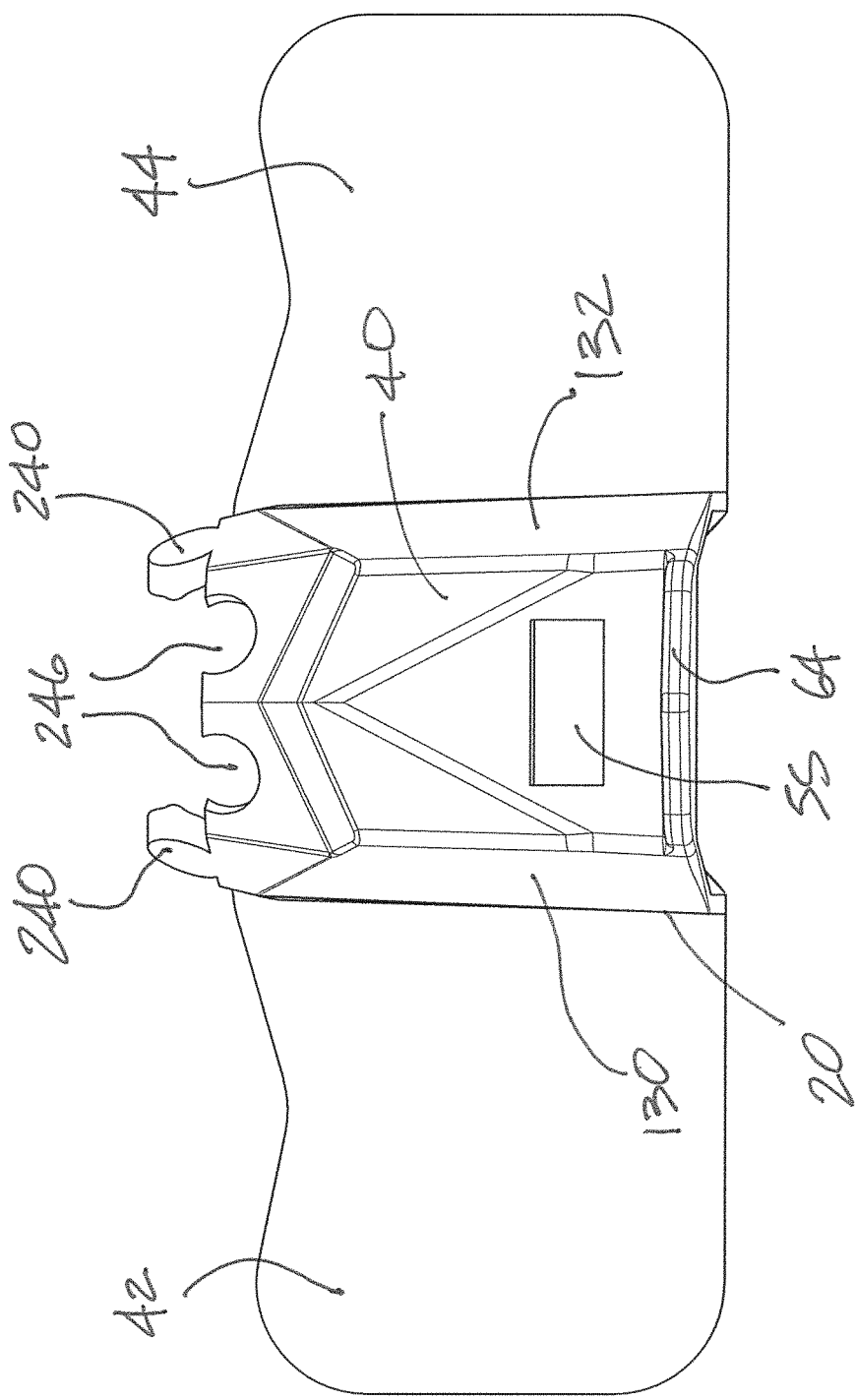

CAPS FOR NEEDLES AND CATHETERS

FIELD OF ART

The disclosed invention generally relates to medical devices such as introducer needles and over-the-needle catheters and, more particularly, to needles and catheters with cap covers for covering the needles prior to use, wherein the cap covers incorporate stabilization platforms for securing the catheters after successful venipuncture.

BACKGROUND

Catheters are commonly used for a variety of infusion therapies, including infusing a patient with fluids, withdrawing blood from a patient, or monitoring various parameters of the patient's vascular system. Catheters are typically connected to a catheter adapter that accommodates the attachment of IV tubing to the catheter. Needles use with catheter tubes have sharp tips that are typically covered by a cap during packaging of the catheter assemblies. The sharp tip of such a needle poses a safety hazard that is often overcome by the inclusion of a removable cap that covers the needle tip and at least part of the assembly, in a thermoplastic wrap or a vacuum pack. After removal from the packaging material, the cap is often removed and discarded. Following placement of the catheter tube into the vasculature of a patient and after or before the catheter hub is connected to an IV fluid source, the hub is secured to protect the access site from inadvertent movement, such as by taping the catheter hub to the patient's skin.

SUMMARY

Aspects of the present disclosure are directed to a needle assembly comprising a needle having a needle shaft attached to a needle hub; and a protective cap located over the needle shaft comprising a first section and a second section; said first section having a bore having the needle shaft located therein and said second section comprising a base covering at least part of the needle hub; and a frangible section formed between the first section and the second section; and wherein the frangible section is severable to separate the first section from the second section.

Another aspect of the present disclosure is directed to a needle assembly comprising a needle attached to a needle hub and a protective cap located over at least part of the needle and wherein the protective can be separated into at least two different sections, a first section and a second section, along a detachment line and wherein one of the two sections can be re-used as a securement device.

The needle assembly can comprise a catheter hub attached to a catheter tube and wherein the needle shaft of the needle projects through the catheter tube.

The catheter hub can comprise an opening or a projection and wherein the cap can comprise the other one of the opening or the projection. The projection can project through the opening. The projection can comprise a mushroom head, an arrow, a barb, or a rotatable tab.

Stabilization elements can be incorporated and folded over the second section of the protective cap. An adhesive pad can attach to each stabilization element. Each adhesive pad can include a release layer.

When two stabilization elements are folded, an adhesive can be included to keep the folded ends in the folded position or the stabilization elements can be sufficiently pliable and flexible to remain folded without aid of an adhesive.

A needle guard can be located inside the catheter hub. The needle guard can include a proximal wall with an opening and two arms. The two arms can cross and the two arms can each include a distal wall.

The second section of the cap can have two side walls and a top wall having a tapered distal end section. The top wall can be flat, can include a texture, can include angles, can include ribs, or combinations thereof.

The first section of the protective can include an elongated tube or cylindrical portion and an expanded or enlarging proximal body portion. The elongated tube and enlarging proximal body portion can have a bore for accommodating a needle.

The needle assembly can further comprise an adhesive pad formed in a U shape with a portion of the adhesive pad can attach to the stabilization elements.

The needle assembly can include wings that have adjustable portions, such as portions that can be trimmed or detached to change the size of the wings.

The needle assembly can include means to attach the first section to the second section at a detachment line. The means can include perforations, weakened portions, or one or more mechanical inter-engagements. The detachment line can be straight, can be curved, or can undulate. The mechanical inter-engagement, which may also be referred to as a joining device, can comprise a combination of projections and receptacles or a combination of tabs and receptacles, similar to interlocking tabs on jigsaw puzzles. The projections can be stubs, a rounded section, or a semispherical section.

In some examples, the receptacles can be formed on a tab and the tab can extend out a proximal end of the first section or can extend out a distal end of the second section.

A glider can be used to help guide the tabs into engagement with the receptacles. The glider can be formed with the first section. The second section can slide on the glider when engaging the tabs and the receptacles of a joining device.

In an example, the detachment line, when separating the first section from the second section, can have remnants of a teared or ruptured surface. In other examples, the detachment line can have a clean edge, such as an edge formed by molding. For example, when the joining device is separated to separate a first section from a second section, the edges on the first and second sections can be clean and can be without traces or remnants of a teared or ruptured surface.

The wings can be unitarily formed to the base portion of the second section or separately formed and subsequently attached to the base portion, such as be welding or by gluing.

In some examples, when a first section is separated from a second section, the proximal end of the first section can have tabs extending proximally thereof. In other examples, the proximal end of the first section can have tabs each with at least one receptacle extending proximally of the proximal end.

Aspects of the present disclosure are further directed to a needle assembly comprising a catheter hub; a catheter tube extending from a distal end of the catheter hub; a needle disposed at least in part in the catheter tube; a needle hub attached to the needle; a needle cap placed over the needle and the catheter tube; said needle cap comprising a first section and a second section, said first section comprising an elongated sleeve having a bore and said second section comprising base portion comprising an upper opening and a lower opening and covering at least a part of the catheter hub; at least one stabilization element extending laterally of the base portion; and wherein an engagement element on the catheter hub is sized and shaped to extend through the upper opening of the base portion after the first section separates from the second section along a detachment line.

The needle assembly can further comprise an adhesive pad attached to the at least one stabilization element.

The needle assembly wherein the at least one stabilization element can be a first wing and wherein a second wing extending from the base portion can be incorporated.

The needle assembly can further comprise a tab on a proximal end of the second section sized and shaped to aid in removing the second section from the catheter hub.

The needle assembly can further comprise an adhesive pad formed in a U shape with a portion of the adhesive pad attached to each of the two wings.

The needle assembly wherein the upper opening of the second section can be a slot.

The needle assembly wherein the engagement element can comprise a hook.

The needle assembly wherein a joining device can join the first section to the second section at the detachment line.

The needle assembly wherein the joining device can comprise two or more projections engaging two or more receptacles or two or more tabs engaging two or more receptacles.

The needle assembly wherein the detachment line can be strait or undulating.

The needle assembly wherein the joining device can be guided by one or more glider.

The needle assembly wherein the receptacles can be located on a tab extending at a proximal end of the first section.

Yet an additional feature of the present disclosure is a method of stabilizing a puncture site comprising separating a first section from a second section of a protective cap along a detachment line; said first section comprising an elongated sleeve having a bore and said second section having a base portion comprising two side walls and a top wall; placing the second section over a catheter hub so that the base portion of the second section covers at least part of the catheter hub; and Using adhesive to secure the base portion from inadvertent movement.

The method can further comprise securing two wings extending laterally of the base portion with adhesive.

The method can further comprise placing a tab on the catheter hub through a slot on the base section.

The method wherein the adhesive can be applied to each of the two wings.

The method wherein the detachment line can be a frangible section located between the first section and the second section.

The present disclosure is further directed to a method of manufacturing a needle assembly as disclosed elsewhere herein.

A yet additional feature of the present disclosure includes a needle assembly comprising: a needle having a needle shaft attached to a needle hub, said needle shaft comprising a needle tip; and a protective cap located over the needle shaft comprising a first section and a second section; said first section having a bore having the needle shaft located therein and said second section comprising a base covering at least part of the needle hub; and a detachment line formed between the first section and the second section; and wherein the detachment line is a weakened section configured to be severable to separate the first section from the second section.

Yet another aspect of the present disclosure includes a method of stabilizing a puncture site. The method can comprise: separating a protective cap into a first section and a second section along a detachment line; said first section comprising an elongated sleeve having a bore and said second section having a base portion comprising two side walls and a top wall; placing the second section over a catheter hub so that the base portion of the second section covers at least part of the catheter hub; and using adhesive to secure the base portion from inadvertent movement.

BRIEF DESCRIPTION OF THE DRAWINGS

These and other features and advantages of the present devices, systems, and methods will become appreciated as the same becomes better understood with reference to the specification, claims and appended drawings wherein:

FIGS. 9A-9D show an alternative protective cap in different views and different sections.

FIGS. 10A-10D show an alternative protective cap in different views and different sections.

DETAILED DESCRIPTION

The detailed description set forth below in connection with the appended drawings is intended as a description of the presently preferred embodiments of needle assemblies having caps with stabilizing features provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1A:
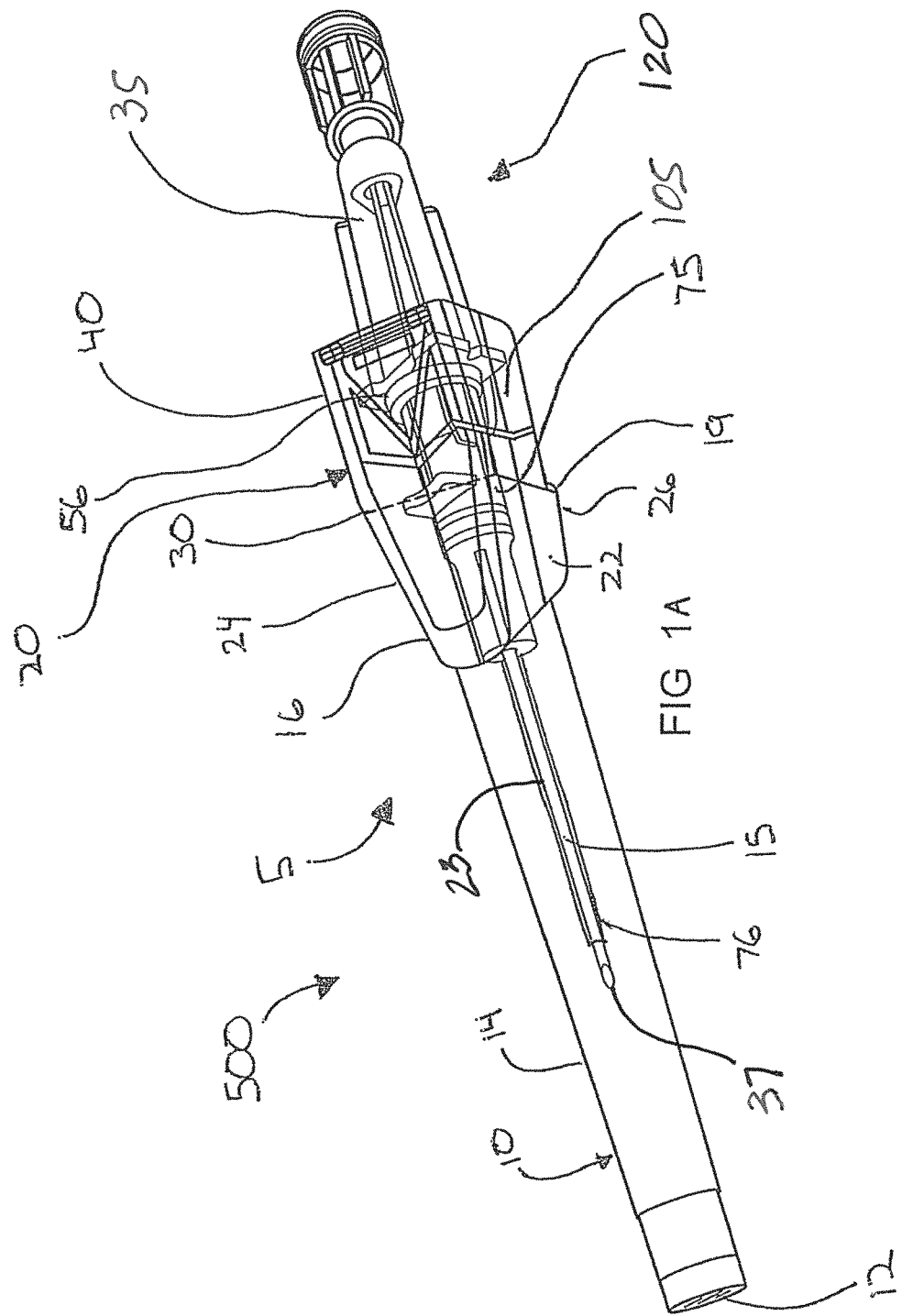
FIG. 1A shows a perspective view of the device with the protective cap still attached.

FIG. 1A shows a perspective view of a needle assembly 500, which comprises an over-the-needle catheter assembly 120 and a cover or cap 5, which is typically frictionally engaged and/or positively engaged to the catheter assembly and removable therefrom. The cover or cap 5 may be used to cover a needle 15 having a sharp tip or distal tip 37 and acts as a protective cap to shield the needle 15 until use. In an example, the cover 5 can include two or more sections 10, 20 that are joined together, such as being integrally formed or mechanically secured to one another. A first section 10 generally covers a needle 15 and a catheter tube 76 of the catheter assembly 120 when placed thereover prior to use, such as during packaging of the assembly in a plastic wrap or a vacuum pack. The needle 15 has a needle shaft 23, a tip 37, and optionally a change in profile, such as a crimp or a bulge near the needle tip 37 for interacting with a needle guard.

A second section 20 of the cap 5 is attached to the first section 10 and covers a catheter hub 75, or at least part of the catheter hub, and can engage or frictionally grips the catheter hub 75 to secure the cap 5 to the catheter assembly 120. In some examples, the second section 20 can grip a flange or a tab on the needle hub 35. As further discussed below, the second section 20 may be referred to as an anchor or a securement device and the first section 10 may be referred to as a protective sleeve. Following removal of the cap 5 from the catheter assembly 120, the two sections 10, 20 can be separated or detached from one another at a detachment line 30, which is located between the distal end and the proximal end of the cap 5. The detachment line 30 can be frangible or a weakened section and configured to readily tear or separate under relatively low force. The detachment line 30 may be a perforation, a thin section that is weaker than the rest of the cover, a groove, or any other structural design that causes inherent weakness to the structural integrity of the cap and, when a sufficient level of force is applied, breaks apart into at least two separate sections 10, 20. The detachment line 30 can be linear or straight, curved, zig-zag, or combinations thereof. Alternatively, as further discussed below, the at least two separate sections 10, 20 can removably connect using a snap fit arrangement, a meshing arrangement, a detent arrangement, or combinations thereof and the detachment line 30 between the two sections 10, 20 can separate by undoing the snap fit, separating the meshing arrangement, or separating the detents.

In some examples, a needle guard can be located inside the catheter hub 75 for covering the needle tip 37 upon retraction of the needle 15 from the catheter hub and the catheter tube 76, such as following successful venipuncture. An exemplary needle guard can comprise a proximal wall having a perimeter defining an opening, two arms extending distally of the proximal wall, and a distal wall located on each arm for blocking the needle tip. The two arms can intersect one another when viewed from a side, in both a ready position where the assembly is ready for use on a patient and a protective position where the needle guard covers the needle tip to prevent inadvertent needle sticks. The needle guard can interact with the change in profile on the needle shaft. For example, when the needle is retracted from the catheter hub following successful venipuncture, the change in profile can engage the perimeter on the proximal wall to retract the needle guard away from the catheter hub. In some examples, the cap 5 is used with a needle device without a catheter tube, such as a hypodermic needle or an epidural needle. Exemplary needle guards usable with the needle assembly 500 of the present disclosure include those disclosed in U.S. Pat. No. 8,647,313, the contents of which are expressly incorporated herein by reference as if set forth in full.

The first section 10 of the cap 5 is generally elongated and has a bore for receiving and covering the needle 15 and the catheter tube 76, protecting a user from accidental needle sticks prior to use and/or for protecting the plastic wrap when the needle device 500 is located inside the package. As shown, the first section 10 is generally cylindrical in cross-section but can embody other shapes, such as being tapered, oval, complex, irregular, polygonal, etc. A distal tip 12, also sometime referred to as end, of the first section 10 is shown, which is configured to cover the tip of the needle, with a planar wall surface with one or more optional openings for venting. A body portion 14 of the first section 10 is sized and shaped to cover the length of the needle 15 and the catheter tube 76. The length of the first section 10 can be longer than the length of the needle 15 projecting out of the catheter hub 75 to ensure adequate clearance, spacing or gap with the needle tip 37. When a relatively longer length is employed for the first section 10, it will allow the cap 5 to be used on different assemblies having different needle lengths. In some examples, the cover 5 is configured to cap or house a needle without a catheter tube, such as an injection needle or an epidural needle. The exact portion of the length of the needle and catheter tube that the body portion 14 covers can vary and can depend on various design factors. In one embodiment, the diameter of the body portion 14 is generally constant along its longitudinal axis. In other embodiments, the diameter may taper away from or toward the distal tip 12. The body portion 14 of the cap 5 has a proximal body portion 16 that transitions the body portion 14 from a smaller diameter section at a distal end 18 (FIG. 2) to an enlarged cross-sectional area at a proximal end 19, which is attached to the second section 20 of the cap 5, as further discussed below. Thus, as shown, the first section 10 of the cap 5 has an elongated body portion or elongated sleeve 17 and a proximal body portion 16, which has a distal end 18 and a proximal end 19.

In some examples, the proximal body portion 16 includes a shoulder 33 (FIG. 2) at the distal end 18 of the proximal body portion. The shoulder 33 steps up to a larger cross-sectional dimension, and the dimension of the larger portion remains constant to the proximal end with varying dimensions contemplated. In the embodiment with a tapered proximal body portion 16, the taper begins at the distal end 18 of the proximal portion. From that point, the inner and outer dimensions of the taper increase along the longitudinal axis of the proximal body portion 16 until they match that of a base portion 40, sometimes refers to as simply "base," of the second section 20 (FIG. 2), discussed below. The tapered proximal body portion 16 has two side walls 22, 24 that transition from vertical to horizontal on the top 122, meeting at a seam 124, with an opening 26 (FIG. 1A) located opposite the top 122. In some examples, the seam 124 is merely a raised section or an apex line at the top 122. In other examples, the seam is omitted or not noticeable.

This configuration of the side walls 22, 24 with an open underside 26 is configured to accommodate attachment and removal of the cover 5 to and from the rest of the catheter assembly, such as to detach from the engagement with the catheter hub 75, the needle hub 35, or both.

The second section 20 generally covers the catheter hub 75 and optionally part of the needle hub 35 when positioned over the catheter assembly 120. In addition to covering the catheter hub 75, the second section 20 has an additional function not recognized, appreciated or disclosed by any known prior art. In the present disclosure, the second section 20, in addition to serving as a cover for the catheter hub and/or needle hub, doubles as a stabilization platform. The second section 20 has a base portion 40 sized and shaped to cover the catheter hub 75, a top surface section or upper panel 56, and an opening 105 (FIG. 5) opposite the top surface section 56. In other embodiments, the base portion 40 is of sufficient dimension to cover the needle hub 35, the catheter hub 75, or all, or part, of both. Following successful venipuncture and the catheter tube 76 is placed inside a vein, the second section 20 can separate from the first section 10 and can again be placed over the catheter hub 75, without the first section 10, to stabilize the puncture site. The second section 20 can be equipped with an adhesive, be applied with an adhesive, or both to anchor the hub, such as a needle hub or a catheter hub, within the second section 20 and against or to a patient. When used with a needle without a catheter tube, such as a Seldinger needle with a needle hub, the second section 20 may be placed over the needle hub to stabilize the needle hub.

Figure 1B:
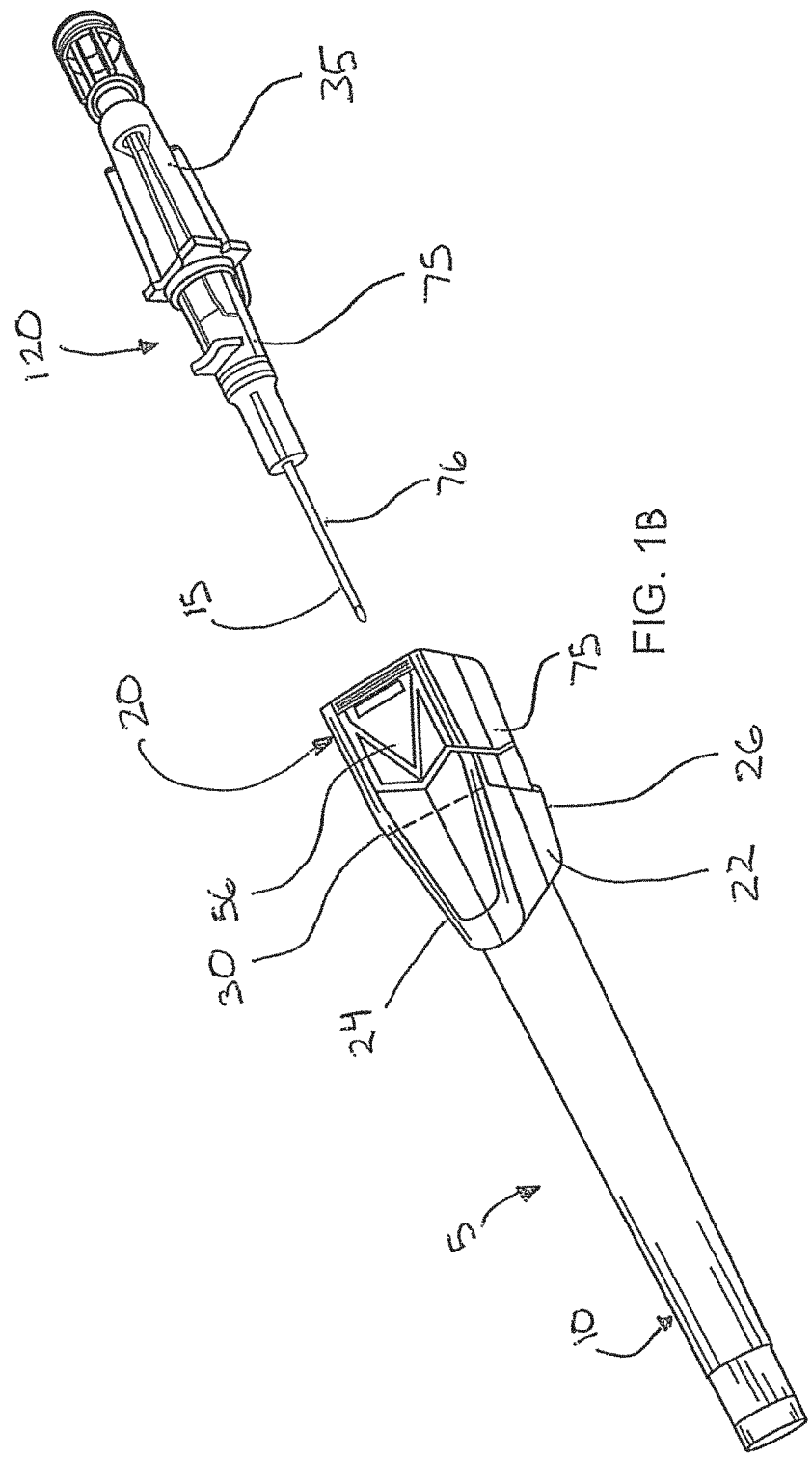
FIG. 1B shows a partially exploded perspective view of the device of FIG. 1A.

FIG. 1B shows the cap 5 separated from the catheter assembly 120 of FIG. 1A, such as prior to using the catheter assembly. The needle 15, needle hub 35, catheter tube 76 and catheter hub 75 remain connected for venipuncture. The cap 5 of FIGS. 1A and 1B may include wings or stabilizing elements 42, 44 extending laterally of the second section 20, as further discussed below.

Figure 2:
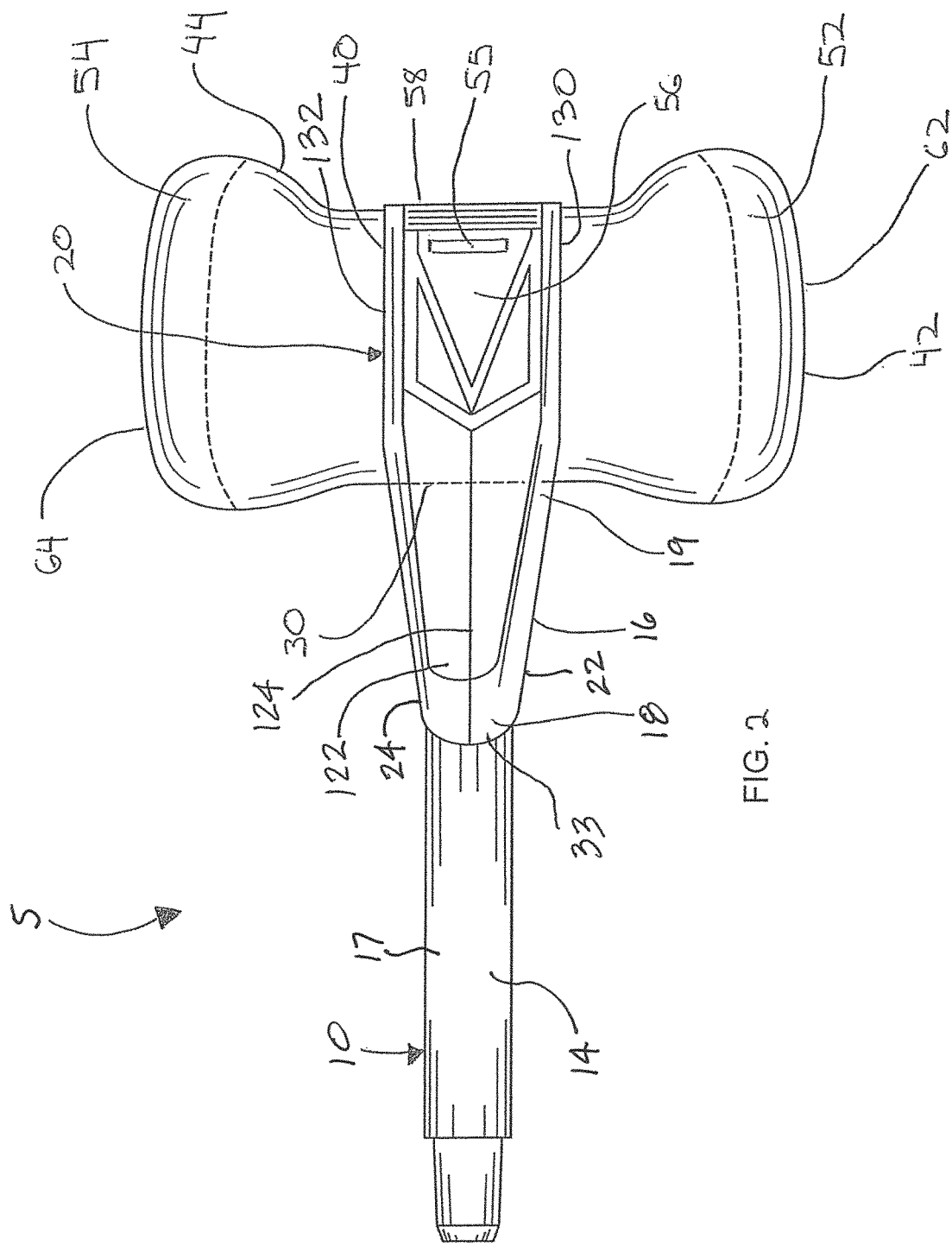
FIG. 2 shows a top view of the device with stabilization elements.

FIG. 2 shows a top view of the cover 5 of FIGS. 1A and 1B with wings 42, 44. A detachment line 30 is visible at the juncture between the proximal body portion 16 of the first section 10 and the base portion 40 of the second section 20. In the embodiment shown, the detachment line 30 is a perforation formed during injection molding to form the cover, which may be made from any number of known thermoplastics and typically with a semi-opaque finish with a transparent cap or an opaque cap contemplated. The perforation line can alternatively be formed in a post-molding process, such as using laser technology to weaken a section of the protective cap to facilitate separation. In some examples, the detachment line 30 comprises a weakened section, such as a thin section, that readily tears to separate the first section 10 from the second section 20. In still other examples, as further discussed below, the first and second sections 10, 20 can be detached along the detachment line by removing or undoing a mechanical inter-engagement. Incorporating the detachment line 30 allows a user to easily separate the first section 10 from the second section 20 by physical means, such as by shearing, tearing, deforming, cutting, un-doing, removing, or twisting. The detachment process will be discussed in more detail below.

Extending laterally from the two sides 130, 132 of the base portion 40 are stabilization elements 42, 44, which may also be called wings. In an example, the stabilization elements 42, 44 are flat and flexible so that they can fold around the base section 40 when packaged in a flexible wrap and unfold to form anchor points for taping the second section 20 over the catheter hub to a patient with one or more pieces of medical tape, as further discussed below with reference to FIG. 8. The stabilization elements 42, 44 may be embodied as wings with any number of features formed thereon, including openings or holes, bumps or protrusions for gripping, and/or design features for aesthetic appeal. As an alternative or in addition to using external or separate medical tape, each stabilization element 42, 44 may incorporate an adhesive layer 46 (FIG. 3) on a bottom surface 48 (FIG. 3) of each of the elements 42, 44 with peelable release layer or be without any adhesive layer. The flexibility of the stabilization elements 42, 44 allows them to be folded over the base portion 40, such as to fold and wrap over the top surface of the second section 20 around the lengthwise axis of the cap during packaging and storage of the catheter assembly, as will be discussed further below. In other embodiments, the stabilization elements 42, 44 are relatively firmer, stiffer, or rigid so that they do not fold over the second section 20 during packaging and storage. Instead, the flexible wrap can be sized and shaped to receive the assembly with the wings in the extended state as shown. In still yet other embodiments, the stabilization elements are omitted and the medical tape is applied directly over the base portion 40 of the second section 20 without any stabilization elements. In another embodiment, the stabilization elements or wings 42, 44 are made up of soft material without any adhesive material. In yet another embodiment, the securement device 20 and the wings 42, 44 are made up of single soft material, molded together in one piece, such as from a soft plastic. The singularly formed securement device 20 and wings 42, 44 made from a soft material allow the two to bend, flex, or otherwise be pliable to fit to the medical device or against the patient. In yet another embodiment, the securement device and the wings are made up of single hard material such as hard plastic, molded together in one piece. Each wing 42, 44 can be formed as a one-piece structure formed to the base portion 40 or from two or more pieces that are joined together using adhesive, welding, or other joining techniques.

Figure 7:
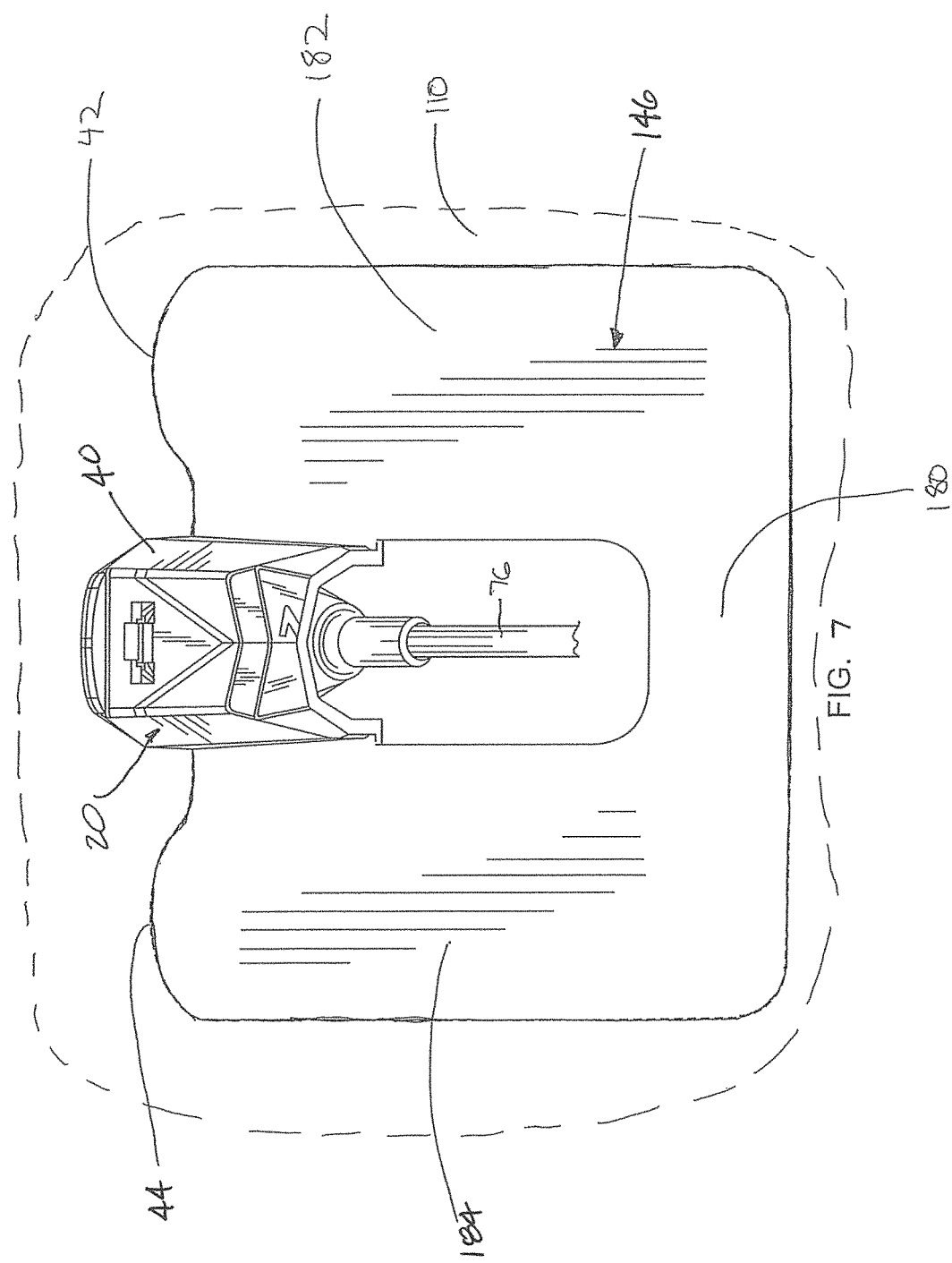
FIG. 7 shows a perspective view of an embodiment of the device with a dressing.

The wings 42, 44 may be formed of any size and shape that will allow a user to tape or otherwise secure the wings 42, 44 to a patient 110 (FIG. 7). In the embodiment shown, the wings 42, 44 can optionally include frangible or adjustable portions 52, 54 along or near the outer edges 62, 64 of each stabilization element 42, 44. The wing frangible or adjustable portions 52, 54 allow the wings 42, 44 to be resized, such as to reduce in area, to match the size of the area on the patient or the size of the patient where the catheter is placed. In still other embodiments, the wings 42, 44 may include several rows of frangible lines or adjustable lines to permit re-sizing options depending on which frangible line is selected for separation. For embodiments without any wings, tape can be directly applied to the base portion 40 of the second section 20. A slot or opening 55 (FIG. 2) is provided on a top surface portion or upper panel 56 of the base portion 40, near a proximal end 58 of the base portion 40. The slot or opening 55 is configured for mechanical engagement between the second section 20 and the catheter hub 75, as will be discussed in more detail below.

Figure 3:
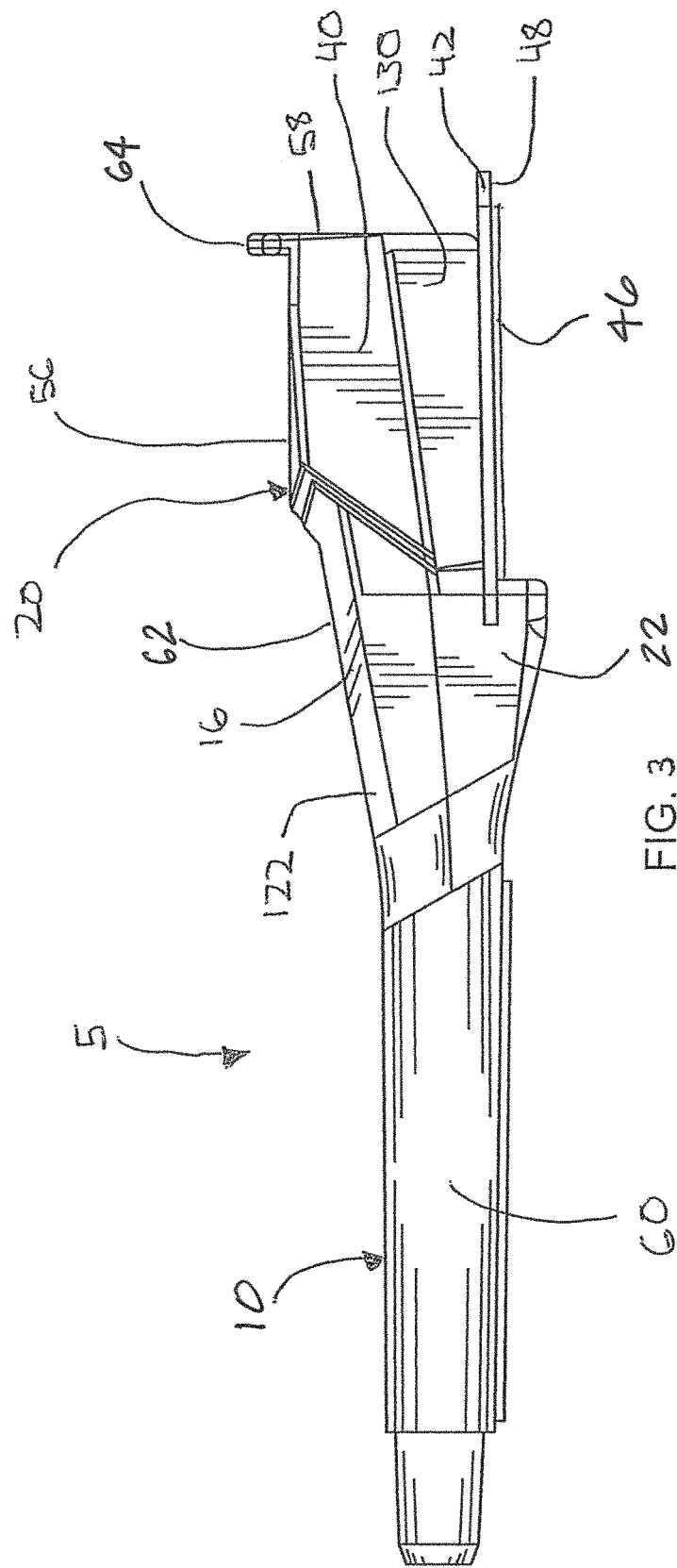
FIG. 3 shows a side view of the device of FIG. 2.

FIG. 3 shows a side view of the cover 5 of FIG. 2. Shown in this view of the cover 5 is a first side wall 22 of the proximal body portion 16 of the first section 10, which has wall surfaces that taper outwardly from the lengthwise axis and from the largest outside dimension of the tube portion 60. The tapered proximal body portion 16 includes a corresponding second side wall 24 (FIG. 1A) on the opposite side. The first side wall 22 of the tapered proximal portion 16 transitions to the top surface 122 of FIG. 3, which is connected to the second side wall 24. At the top surface 122, a ridge 62 is provided, which defines a centerline of the top surface running along the lengthwise axis. An upper panel 56, which can be flat or has a curved portion, is located at a proximal end of the second section 20 that forms the top of the base portion 40. A tab 64 is formed on the flat panel 56 at the proximal end 58, which in one example embodies a vertical wall with a tapered wall contemplated. The tab 64 provides leverage for a user to grip in the removal of the cover 5 from the catheter assembly or needle device before use. The tab 64 can also provide a user with some additional leverage in separating, urging, freeing, and/or rotating the proximal body portion 16 of the first section 10 clear of the catheter assembly for removal of the cap from the catheter assembly. In addition, the tab 64 can provide stability to the stabilization elements 42, 44 when they are folded over the top panel 56 of the base portion 40 of the second section 20 during packaging and storage. In other embodiments, the tab 64 may be omitted, made taller, shorter, wider, or have other shapes and curvatures. The adhesive pad 46 shown with stabilization element 42 has a removable liner, such as a release layer, to protect the adhesive, as is well known in the art. In other embodiments, the adhesive pad 46 may be omitted and medical tape may instead be used to adhere the stabilization elements 42, 44 (FIG. 2) to a patient. In still other embodiments, a dressing may be used in place of the medical tape or in combination therewith. The dressing is discussed in more detail below.

Figure 4:
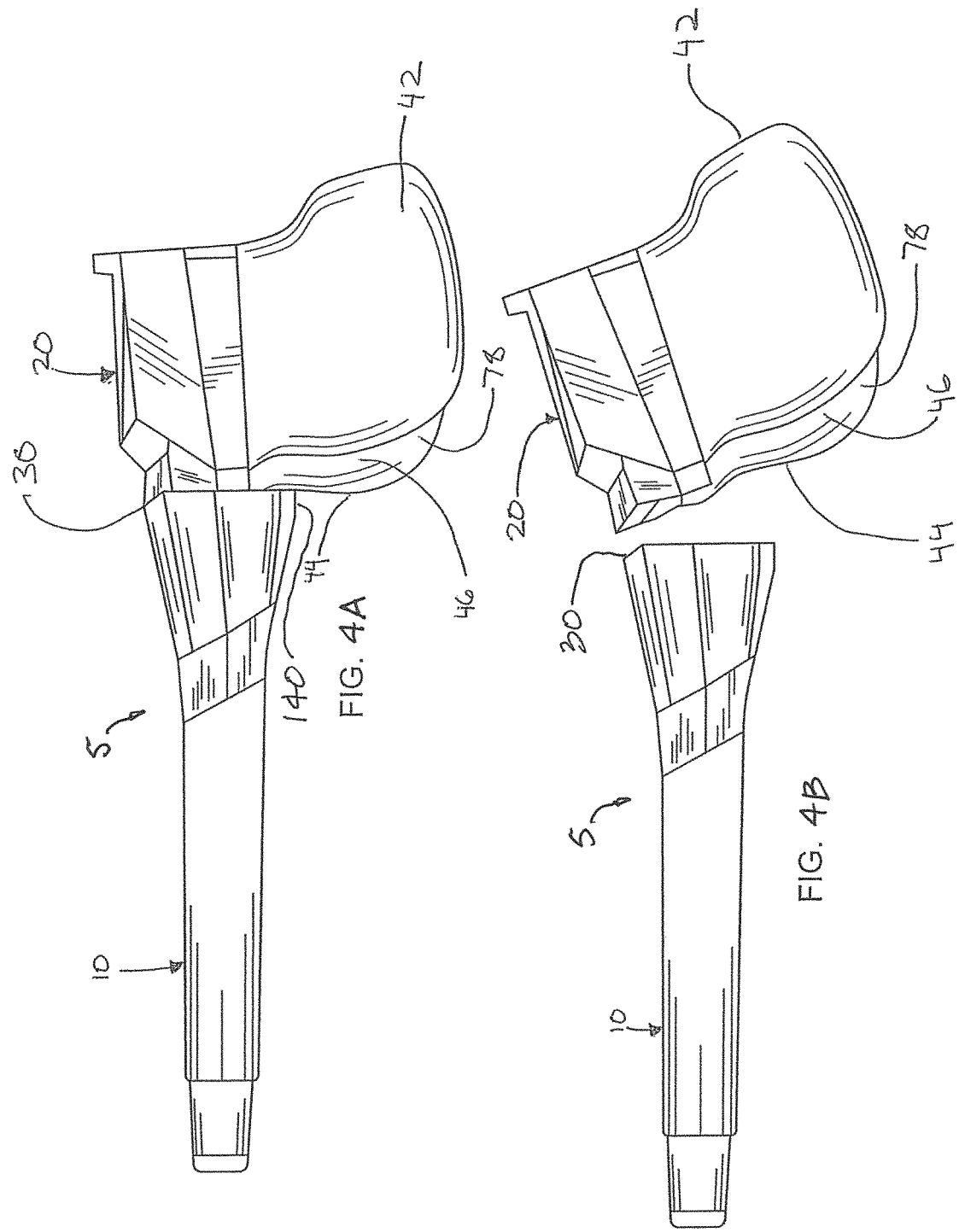
FIG. 4A shows a side view of an embodiment of the device just before separation.
FIG. 4B shows a side view of an embodiment of the device after separation.

FIG. 4A shows the cap 5 after removal from the needle and catheter hub and FIG. 4B shows the first section 10 of the cap 5 separated from the second section 20 at the detachment point or line 30. After successful venipuncture using the catheter assembly 120 of FIGS. 1A and 1B and the needle and needle hub removed from the catheter tube and catheter hub, the cap 5 may be used to stabilize the catheter hub 75 on the patient to stabilize and/or secure the catheter hub and the puncture site. As shown in FIG. 4B, the cap 5 is separated into two sections 10, 20 along the detachment line 30. The detachment line 30 is frangible and configured to readily tear or separate. The detachment line 30 may be a perforation, a thin section that is weaker than the rest of the cover, a groove, or any other structural design that will cause inherent weakness and, when a sufficient level of force is applied, break or sever at the detachment line into two separate sections 10, 20. The first and second sections 10, 20 may alternatively be mechanically secured to one another at the detachment line 30 and the two are separable from one another by un-doing, freeing, un-snapping, or otherwise separating the mechanical connection at the detachment line 30. Preferably, the detachment line 30 is configured so that an incidental level of force will not be sufficient to cause breakage or separation of the cap into two sections 10, 20. However, the level of force required to separate the cap at the detachment line 30 may be adjusted without deviating from the scope of the present disclosure, such as by increasing the gaps or lengths between perforations, or increasing or decreasing the material thickness of the weakened section. To cause separation of the two sections 10, 20, a user applies force to increase the tension along the underside 140 of the cap 5. Once the material of the cap 5 begins to tear along the detachment line 30, the user continues to apply force until the detachment progresses to the top of the cap 5. At that point, the user applies force to tear the material along the detachment line 30 across the top of the cap 5. Of course, other methods may be used to sever the first section from the second section, such as using a scissor.

After separation, the first section 10 may be discarded or recycled. The second section 20, with the first section 10 detached therefrom, can be re-used as a securement device. In an example, the second section 20, which comprises a base portion 40, sidewalls 130, and an opening 105 on a side opposite the top surface 56, is sized and shaped to couple with the catheter hub 75 (FIG. 1) to secure the catheter hub following venipuncture. By securing the catheter hub 75, the puncture site can be restricted from unwanted movement caused by movement of the catheter hub. Thus, aspect of the present disclosure includes a portion of a cap 5, which is used during packaging for covering the needle, being retained following removal of the cap from the needle for subsequent use. For example, the second section 20 may be separated from the first portion 10 and retained for re-use, such as by placing the second section 20 over the catheter hub to stabilize the catheter hub. If stabilization elements 42, 44 are included and are folded, they are moved from the folded position to a second, ready-to-use, or extended position as shown in FIG. 4B of FIG. 5. In the present embodiment, the soft adhesive pads 46 provided with the two wings may be used to secure the wings or stabilization elements 42, 44 to the patient, after removing the removable liner 78 from each adhesive pad 46. In other embodiments, the stabilization elements 42, 44 are secured to the patient using external medical tape. In still yet other examples, the second section 20 is secured to the patient using both the adhesive pads 46 on the two wings 42, 44 and external medical tape. The second section 20 may further be secured to the patient using mechanical engagement or connection between the catheter hub 75 and the base portion 40. For example, a tab or a thread on the catheter hub may project through the slot 55 (FIGS. 2 and 5) on the second section 20, which may be called an anchor or securement device, to mechanically engage the two.

Figure 5:
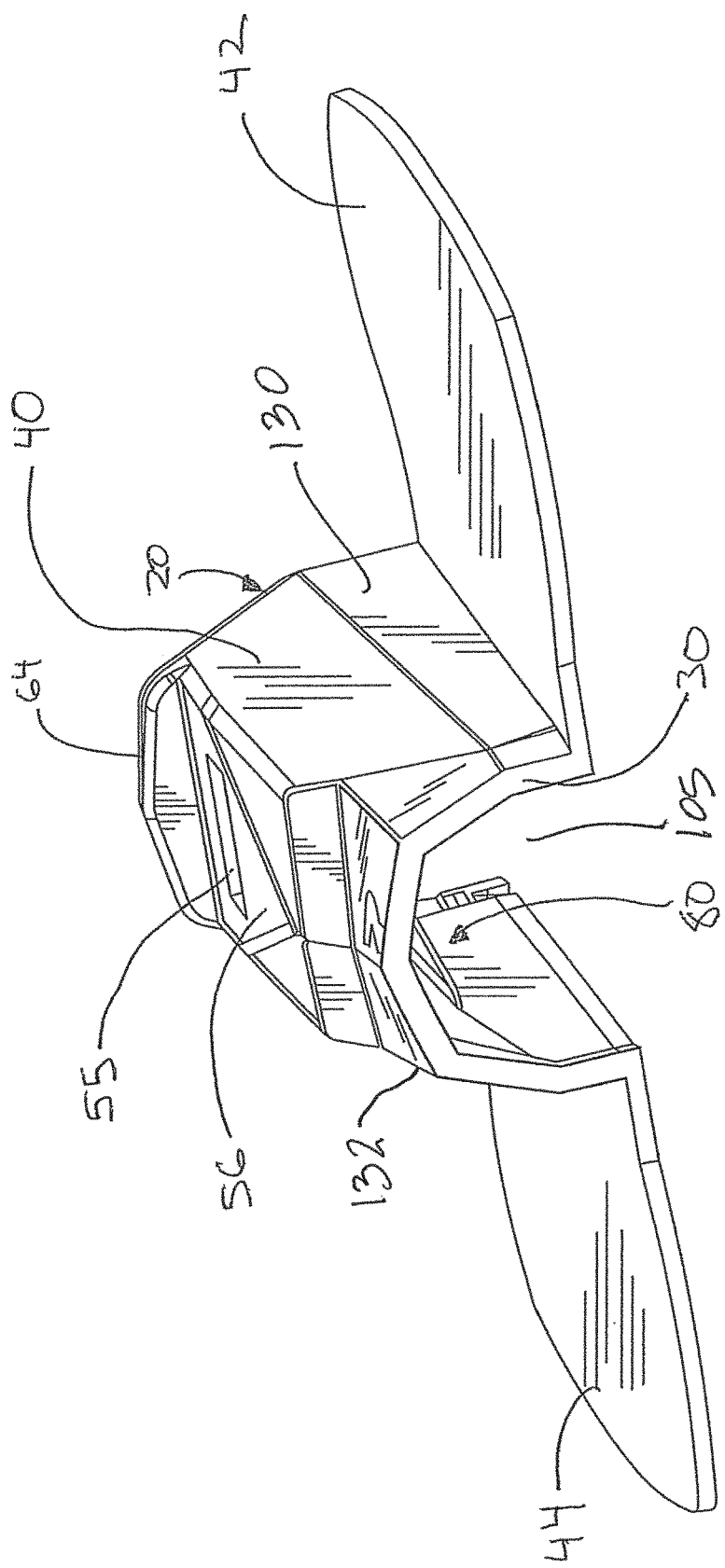
FIG. 5 shows a perspective view of the second section of the device.
Figure 6:
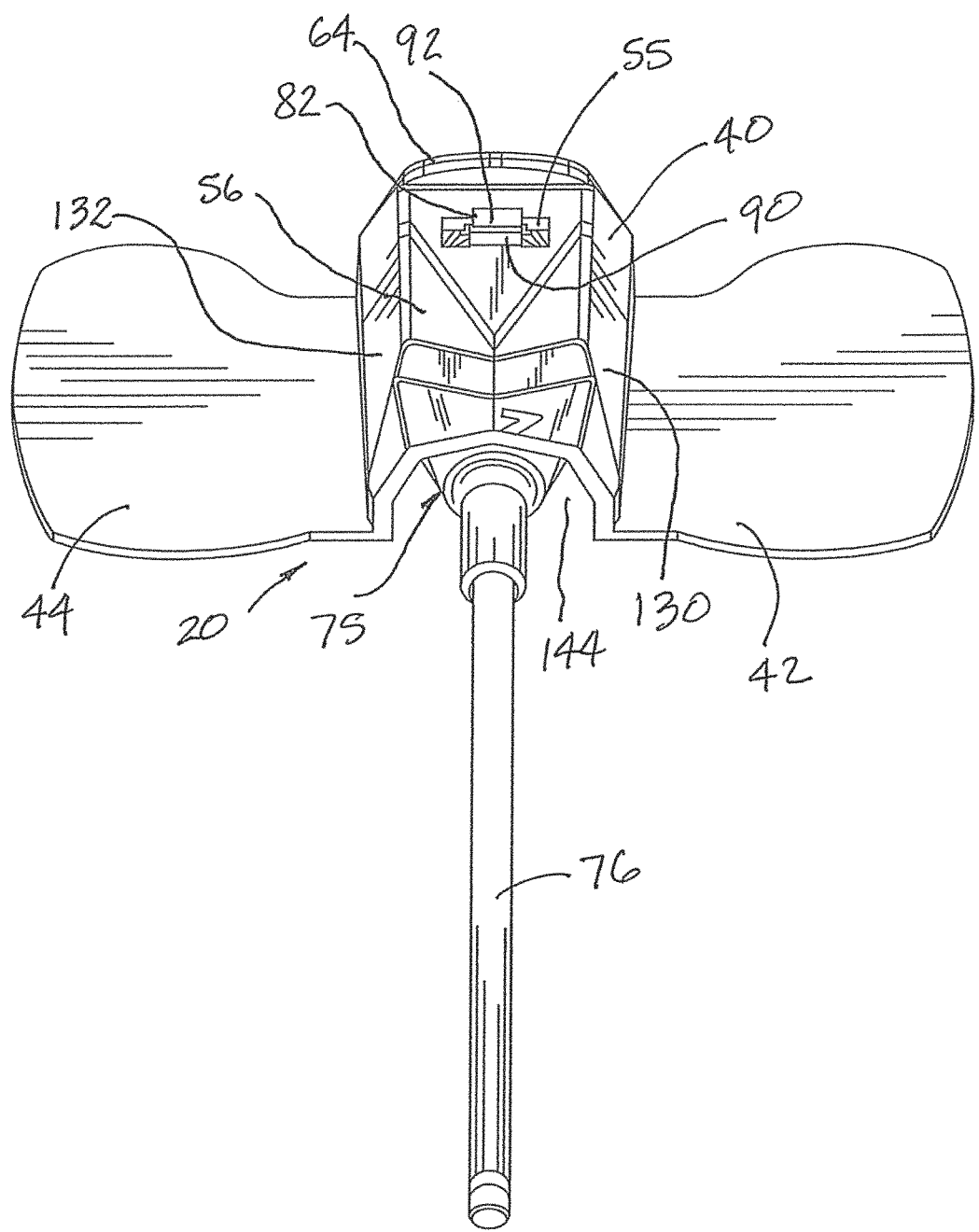
FIG. 6 shows a top view of the second section attached to the catheter hub.

FIG. 5 shows the second section, anchor, or securement device 20 after separation from the first section 10 and oriented with the stabilization elements 42, 44 extending away from the base portion 40 and an opening 105 on the underside of the base portion 40 facing towards the bottom of FIG. 5, generally corresponding to its normal use position when located over a catheter hub 75. FIG. 6 shows the second section 20 placed over a catheter hub 75, such as following successful venipuncture and the catheter tube 76 emplaced into a patient's vein. To ensure that the base portion 40 of the anchor 20 aligns with the catheter hub 75 and the two engage to provide sufficient stability for the catheter hub, the slot or opening 55 on the top surface section 56 of the base portion 40 just distal of the tab 64 can be placed around an engagement element 82, which can be a projection, a tab, rib or threads, formed on the catheter hub 75. In some embodiments, the locations of the slot/opening 55 and projection 82 can reverse with the catheter hub comprising a recess and the base portion 40 comprising a projection for projecting into the recess on the catheter hub. The height of the two sidewalls 130, 132 can be selected so that at least part of the interior wall of the top surface section 56 pushes against the catheter hub 75 to firmly secure the catheter hub within the interior cavity or space 144 of the anchor 20. In other examples, the two sidewalls 130, 132 are selected so that the interior wall of the top surface section 56 does not push against the catheter hub. By placing the second section 20 over the catheter hub 75, the catheter hub is guarded or secured against unwanted movement or at least from excessive movement. In some embodiments, the engagement element 82 can include a simple vertical tab or rib. In another example, the engagement element 82 can comprise a shaped tab comprising two structural members 90, 92. A first member 90 can include a vertical section or base and the second member 92 can include a radially extending section, which can be a slanted section that resembles a rib, a barb or a hook. This allows the engagement member or element 82 to form a more secured mechanical engagement with the slot 55, when the hook 92 is placed through the slot 55. In this manner, the catheter hub 75 is mechanically engaged to the base portion 40 and the securement is not based solely on adhesive or tape.

In other embodiments, the engagement element 82 can include a single "T" shaped element, where a crossbar of the "T" shaped element compresses as it enters the slot 55 and then expands once the crossbar exits the slot 55. Other alternative engagement element 82 might include a shaft extending from the catheter hub 75 capped by a hemisphere structure, similar to a mushroom head. The hemisphere structure would compress radially when entering the slot 55, which can be round, and then expand back out upon exiting the slot. Slits or slots may be provided on the hemisphere structure to facilitate flexing. In still another embodiment, a rotatable latch may be used secure the catheter hub 75 to the anchor 20. In still yet another example, the engagement element 82 is sized so that it frictionally engages the slot 55 or is interference fit within the slot 55.

FIG. 7 shows an alternative embodiment in which an adhesive pad is used to secure the stabilization elements 42, 44 of the anchor 20 to a patient, which can be the same or substantially the same as the anchors discussed elsewhere herein. In the present embodiment, an adhesive pad or dressing 146 in the shape of a "U" may be used to attach the stabilization elements 42, 44 extending from the base portion 40 to the patient 110. The adhesive pad or dressing 146 is in the shape of a "U" with the base 180 of the "U" placed distally of where the catheter tube 76 enters the patient 110. Two sides 182, 184 of the "U" extend proximally from the base 180 and over the stabilization elements or wings 42, 44. In some embodiments, the sides 182, 184 of the "U" shaped pad may be narrower than, the same width as, or wider than the width of the stabilization elements. The two sides 182, 184 should extend sufficiently proximally past the ends of the two wings so that they can contact the patient's skin to more securely hold the wings 42, 44 to the patient. In some embodiments, the dressing 146 is sized and shaped so that it covers all of the stabilization elements 42, 44. In other embodiments, the dressing may leave some of one or both stabilization elements 42, 44 exposed and not covered. In still other embodiments, the dressing 146 might be located short of the side or proximal edges of the stabilization elements 42, 44. Other embodiments might use other shaped dressings, including a "V" shaped dressing, a "D" shaped dressing, or a dressing extending from each of the stabilization elements 42 in any number of shapes, including squares, rectangles, triangles, and semi-circles.

In some embodiments the dressing 146 is made integral with the base portion 40 of the second section or anchor 20 and the stabilization elements 42, such as the wings, can be omitted. For example, the sides 182, 184 of the "U" shaped pad can be pre-affixed to the sides if the base portion 40 of the second section anchor 20. In use, after catheterization, the user separates the two sections 10, 20 of the protective cap 5 and then places the base portion 40 of the second section 20 onto the catheter hub 75 and detaches the release liner 78 from the dressing 146 and attaches the dressing to the patient's skin. The dressing can be made of soft material to provide extra stabilization with larger surface area of contact to the catheter by firmly adhering to the patient's skin. In one example, the sides 182, 184 of the dressing 146 are unfolded from the sides of the base portion 40, the release liners from each side is removed and then applied firmly to the patient's skin.

Figure 8:
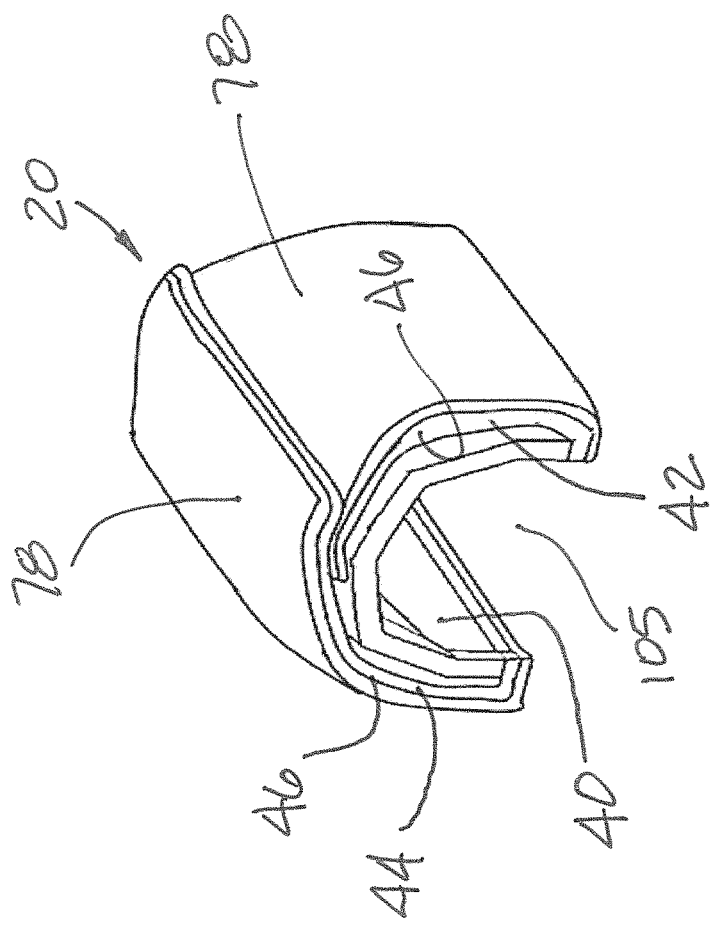
FIG. 8 shows a securement device that is part of a protective cap after removal of a first section of the cap.

FIG. 8 shows an exemplary embodiment of a second section, securement device or anchor 20 separated from a first section 10 and wherein the stabilizing elements 42, 44, such as wings, are folded over the base portion 40 of the second section 20. The stabilizing elements 42, 44 may be folded as shown to facilitate packaging the cap 5 having the anchor 20 of FIG. 8 mounted over a needle device or a catheter assembly. The folded configuration of the wings provides a relatively smaller width profile and therefore a relatively smaller packaging for the needle device. The stabilizing elements 42, 44 are each shown with an adhesive pad 46 and a release liner 78. To stabilizing elements 42, 44 may be flexible and remain in the folded configuration as shown without any restraining or holding means. In other examples, repositionable adhesive or other removable adhesive may be used to hold the far ends of each wings in the folded state.

FIG. 9A shows a protective cap 5 having a first section 10 and a second section 20, similar to other protective caps discussed elsewhere herein. In the present embodiment, the first and second sections 10, 20 may be mechanically secured to one another along or near the detachment line 30 using a joining device. The joining device for joining the first section 10 to the second section 20 may be incorporated interiorly of the cap 5 so that a smooth outer contour is provided externally for aesthetic appeal. In an example, the joining device is sized and shaped to provide a smooth external transition at the two external joining surfaces 220*a*, 220*b*, at or near the detachment line 30. A marker or a trace 232 may be provided on the exterior of the base section 40 to facilitate aligning of the components of the joining device, as further discussed below.

Figure 9B:
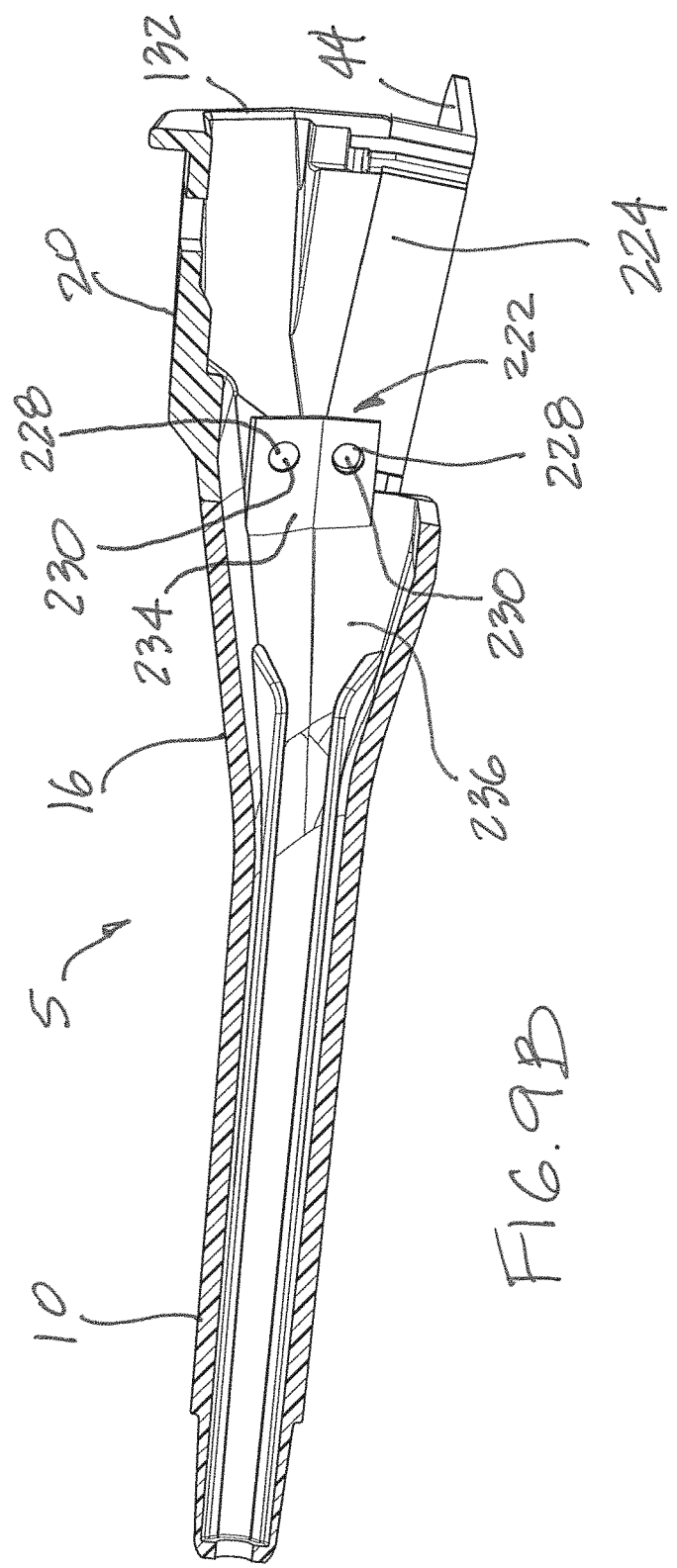

FIG. 9B shows a cross-sectional side view of the cap 5 taken along the lengthwise direction of the cap shown in FIG. 9A. In an example, two joining devices 222 (only one shown) can be provided interiorly of the cap 5. For example, one joining device 222 can be provided on each lengthwise half of the cap, such as along a section of one of the interior sidewalls 224 of the base portion 40 and the interior sidewall 226 of the proximal body portion 16 of the first section 10. The joining device 222 can each include one or more projections 228 for engaging corresponding receptacles 230, similar to a hole and pin or snap-fit configuration. In the example shown, two projections 228 are provided with the base portion 40 for projecting into two receptacles 230 provided with the proximal body portion 16 for each joining device 222. However, the positions of the projections and receptacles can reverse with the projections located with the proximal body portion 16. The engagement between each pair of projection 228 and receptacle 230 can be a close fit, a friction fit, or an interference fit. In an example, the two projections 228 can be formed directly with the interior sidewall 224 of the second section 20 and the receptacles 230 can be provided on a tab or extension 234 extending from an end of the first section 10.

To separate the first section 10 from the second section 20, a user simply spreads the two sidewalls 130, 132 away from one another or compresses the two sidewalls 130, 132 together, depending on whether the projections 228 are located with the base portion 40 or the proximal body portion 16. This will separate the projections 228 from the receptacles 230 to allow the first and section sections 10, 20 to separate from one another at the detachment line 30. Once separated, the second portion 20 may be used to secure a catheter hub, as discussed elsewhere herein.

FIG. 9C shows the first section 10 of the cap 5 shown in FIG. 9A separated from the second section 20.

FIG. 9D shows the second section 20 of the cap 5 of FIG. 9A separated from the first section 10. In an example, the projections 228 embody short pegs or stubs. In other examples, the projections 228 embody a dome section or a partial sphere, as shown in FIG. 9D.

FIG. 10A shows a protective cap 5 having a first section 10 and a second section 20, similar to other protective caps discussed elsewhere herein. In the present embodiment, the first and second sections 10, 20 may be mechanically secured to one another along or near a detachment line 30 using a joining device 222. As shown, the detachment line of the present embodiment can be other than straight, such as curved or undulating. The joining device 222 for joining the first section 10 to the second section 20 may be incorporated within the wall surfaces of the cap 5 and mesh in a way that a smooth contour is provided externally for aesthetic appeal.

In an example, the joining device 222 can comprise a plurality of interlocking tabs 240 engaging a plurality of corresponding receptacles 246 similar to interlocking tabs on jigsaw puzzles. In the example shown, there are four tabs 240 for engaging four corresponding receptacles 246. In other examples, there can be fewer than four tabs 240, such as three or two tabs, or greater than four tabs, such as five or six or more, for engaging the same number of receptacles 246. In an example, a tab each can be incorporated along a side of the cap and two tabs on an upper section 56 of the cap 5.

Figure 10B:
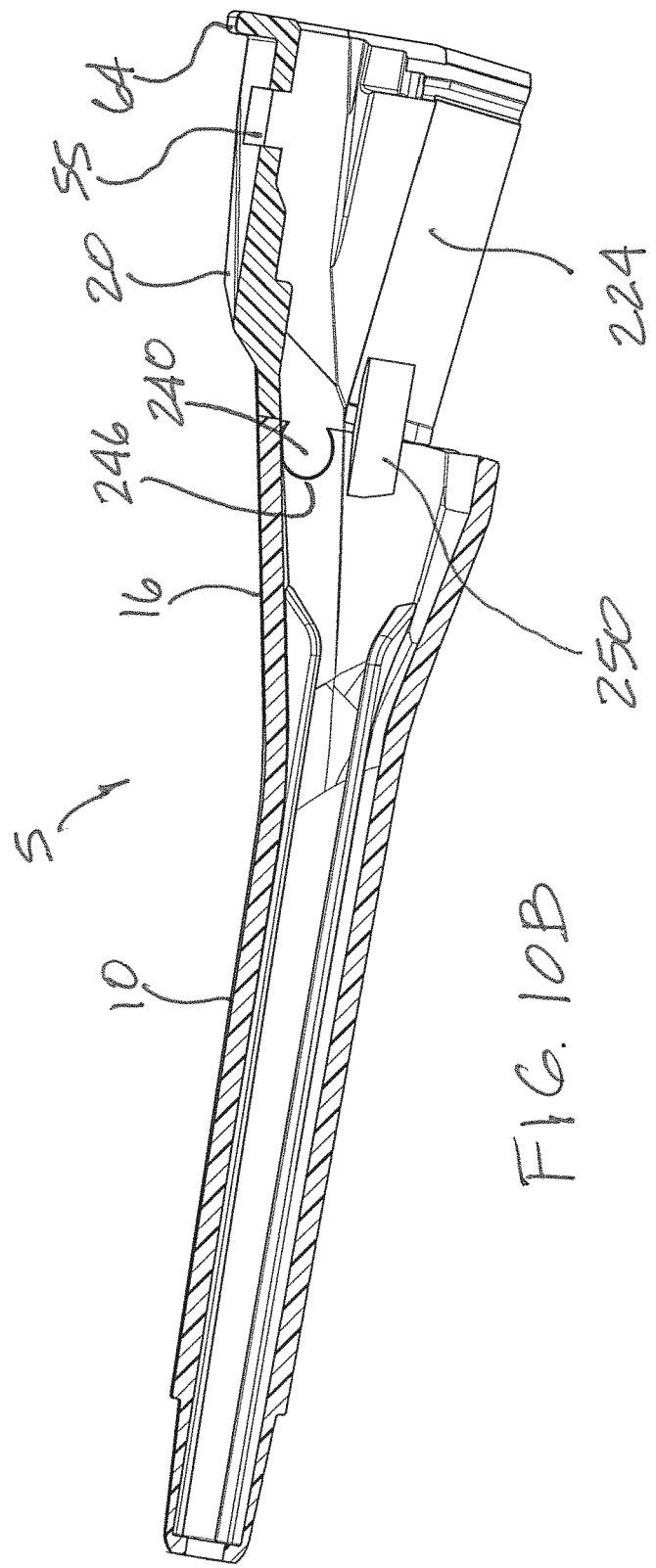

FIG. 10B shows a cross-sectional side view of the cap 5 taken along the lengthwise direction shown in FIG. 10A. In an example, the joining device 222, which comprises a plurality of interlocking tabs and receptacles, can be formed, such as molded, directly at the proximal end of the proximal body portion 16 and the distal end of the base member 40. The tabs and the receptacles can be brought together to mate as shown in FIGS. 10A and 10B.

To facilitate guiding the tabs 240 to the receptacles 246 or vice-versa to assemble the first and second sections 10, 20 together, one or more gliders 250 (only one shown) can optionally be provided interiorly of the cap 5. As shown, a glider 250, which can embody a ramp or a tab, having surface features to guide the tabs and the receptacles is shown. The glider 250 can extend from the first section 10 and presenting a surface for the base member 40 to slide against when meshing the tabs and the receptacles together to join the first and the second sections together. When incorporated, the presence of the gliders 250 also helps to prevent the first section 10 and the second section 20 from moving laterally relative to one another to dislodge or separate the tabs from the receptacles.

To separate the first section 10 from the second section 20, a user simply spreads the two sidewalls 130, 132 of the base member 40 away from one another and the lifting the base member 40 relative to the first section 10, or lower the first section 10 relative to the second section, to separate the two along the departing line 30. This will separate the tabs 240 from the receptacles 246 to allow the first and second sections 10, 20 to separate from one another at the detachment line 30. Once separated, the second portion 20 may be used to secure a catheter hub, as discussed elsewhere herein. In other examples, the first and second sections 10, 20 can simply be pulled in opposite directions to separate the two along the detachment line.

FIG. 10C shows the first section 10 of the cap 5 shown in FIG. 10A separated from the second section 20.

FIG. 10D shows the second section 20 of the cap 5 of FIG. 10A separated from the first section 10.

Methods of making and of using the needle devices and caps and their components disclosed elsewhere herein are within the scope of the present disclosure.

Although limited embodiments of the protective cap and catheter assemblies and their components have been specifically described and illustrated herein, many modifications and variations will be apparent to those skilled in the art. Further, while the cap is described in connection with a catheter assembly, the same cap may be used on other needle devices, such as a hypodermic needle, a Seldinger needle, and an epidural needle, to name a few. Accordingly, it is to be understood that the protective cap and catheter assemblies and their components constructed according to principles of the disclosed devices, systems, and methods may be embodied other than as specifically described herein. The disclosure is also defined in the following claims.

What is claimed is:

1. A needle assembly comprising:
   a catheter hub attached to a catheter tube;
   a needle having a needle shaft attached to a needle hub, said needle shaft comprising a needle tip; and
   a protective cap located over the needle shaft and removable from the needle shaft;
   said protective cap comprising a first section and a second section;
   said first section having a bore having the needle shaft located therein; and
   said second section comprising a base covering at least part of the needle hub; and
   a detachment line located between the first section and the second section of the protective cap configured to separate the first section having the bore from the second section when the detachment line is severed;
   wherein the detachment line comprises a weakened section or a seam held together by a joining connector and is configured to be separable to separate the first section of the protective cap from the second section of the protective cap; and
   wherein said second section is removable from the needle shaft prior to, and following, separation of the first section from the second section; and
   wherein the needle shaft projects through the catheter tube, and wherein said second section is frictionally engaged to the catheter hub.

2. The needle assembly of claim 1, wherein the catheter hub comprises an opening or a projection and wherein the protective cap comprises the other one of the opening or the projection.

3. The needle assembly of claim 2, wherein the projection projects through the opening.

4. The needle assembly of claim 3, wherein stabilization elements extend from the second section.

5. The needle assembly of claim 4, further comprising an adhesive pad attached to each stabilization element.

6. The needle assembly of claim 4, further comprising an adhesive pad formed in a U shape with a portion of the adhesive pad attached to the stabilization elements.

7. The needle assembly of claim 4, wherein the joining connector comprises two or more projections engaging two or more receptacles or two or more tabs engaging two or more receptacles.

8. The needle assembly of claim 1, further comprising a needle guard located inside the catheter hub.

9. The needle assembly of claim 8, wherein the second section comprises two side walls and a top wall having a tapered distal end section.

10. A needle assembly comprising:
    a catheter hub;
    a catheter tube extending from a distal end of the catheter hub;
    a needle with a needle tip disposed at least in part in the catheter tube and the needle tip extending distally of a distal end of the catheter tube;
    a needle hub attached to the needle at an end opposite the needle tip;
    a needle cap comprising a first section and a second section placed over the needle and the catheter tube;
    wherein:
    said first section comprising an elongated sleeve having a bore;

said second section comprising a base portion comprising a lower opening and the base portion covering at least a part of the catheter hub; and said second section being removably attached to the catheter hub and removable from the catheter hub before using the needle for puncturing and mountable over the catheter hub following venipuncture;

at least one stabilization element comprising a planar surface extending laterally of the base portion.

11. The needle assembly of claim 10, wherein the base portion has at least one stabilizing element having a planar surface extending laterally of a central portion, and wherein an adhesive pad is attached to the at least one stabilization element.

12. The needle assembly of claim 11, wherein the at least one stabilization element is a first wing and further comprising a second wing, and wherein the first wing and the second wing extend from the base portion.

13. The needle assembly of 10, further comprising a tab on a proximal end of the second section sized and shaped to aid in removing the second section from the catheter hub before using the needle for puncturing.

14. The needle assembly of claim 12, wherein the adhesive pad is formed in a U shape with a portion of the adhesive pad attached to each of the two wings.

15. The needle assembly of claim 12, wherein the upper opening of the second section is a slot.

16. The needle assembly of claim 12, wherein second section has a slot and wherein a projection on the catheter hub projects through the slot.

17. A method of stabilizing a puncture site comprising:

separating a protective cap into a first section and a second section along a detachment line;

said first section comprising an elongated sleeve having a bore; and said second section having a base portion comprising two side walls, an opening between the two side walls, and a top wall;

placing a catheter hub in the opening between the two side walls of the second section after separating a needle from the catheter hub;

applying an adhesive pad or strip over both the second section and the catheter hub; and wherein a catheter tube having a lumen is attached to and extends distally of the catheter hub.

18. The method of claim 17, further comprising securing two wings extending laterally of the base portion with adhesive.

19. The method of claim 18, further comprising placing a tab on the catheter hub through a slot on the base section of the second section.

20. The method of claim 19, wherein the adhesive is applied to each of the two wings.

21. The method of 20, wherein the detachment line is a frangible section located between the first section and the second section.

* * * * *